(12) United States Patent
Gal

(10) Patent No.: US 9,913,613 B2
(45) Date of Patent: *Mar. 13, 2018

(54) BAND-LIKE GARMENT FOR PHYSIOLOGICAL MONITORING

(71) Applicant: adidas AG, Herzogenaurach (DE)

(72) Inventor: Yoav Gal, Berkeley, CA (US)

(73) Assignee: adidas AG, Herzogenaurach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/361,657

(22) Filed: Nov. 28, 2016

(65) Prior Publication Data

US 2017/0135638 A1 May 18, 2017

Related U.S. Application Data

(63) Continuation of application No. 11/586,026, filed on Oct. 24, 2006, now Pat. No. 9,504,410, which is a continuation-in-part of application No. 11/233,317, filed on Sep. 21, 2005, now Pat. No. 8,034,001.

(60) Provisional application No. 60/730,890, filed on Oct. 26, 2005, provisional application No. 60/699,698, filed on Jul. 15, 2005, provisional application No. 60/611,900, filed on Sep. 21, 2004.

(51) Int. Cl.
| | | |
|---|---|---|
| A61B 5/04 | (2006.01) |
| A61B 5/00 | (2006.01) |
| A41D 13/12 | (2006.01) |
| A61B 5/0205 | (2006.01) |
| A61B 5/0404 | (2006.01) |
| A61B 5/0428 | (2006.01) |

(52) U.S. Cl.
CPC ........ *A61B 5/6831* (2013.01); *A41D 13/1281* (2013.01); *A61B 5/02055* (2013.01); *A61B 5/0404* (2013.01); *A61B 5/04286* (2013.01)

(58) Field of Classification Search
CPC .......................... A61B 5/6831; A61B 5/1135
See application file for complete search history.

*Primary Examiner* — Christian Jang
(74) *Attorney, Agent, or Firm* — Sterne, Kessler, Goldstein & Fox P.L.L.C.

(57) ABSTRACT

This invention provides a physiological monitoring garment having a band-like configuration and incorporating respiratory, cardiac and temperature sensors. The garment is designed so that it is easily constructed from a few number of separate elements, and so that one garment design can be adjusted to subjects of a range of sizes and shapes. The design is further adapted to require little on no wearer effort during donning or wearer attention during use.

21 Claims, 7 Drawing Sheets

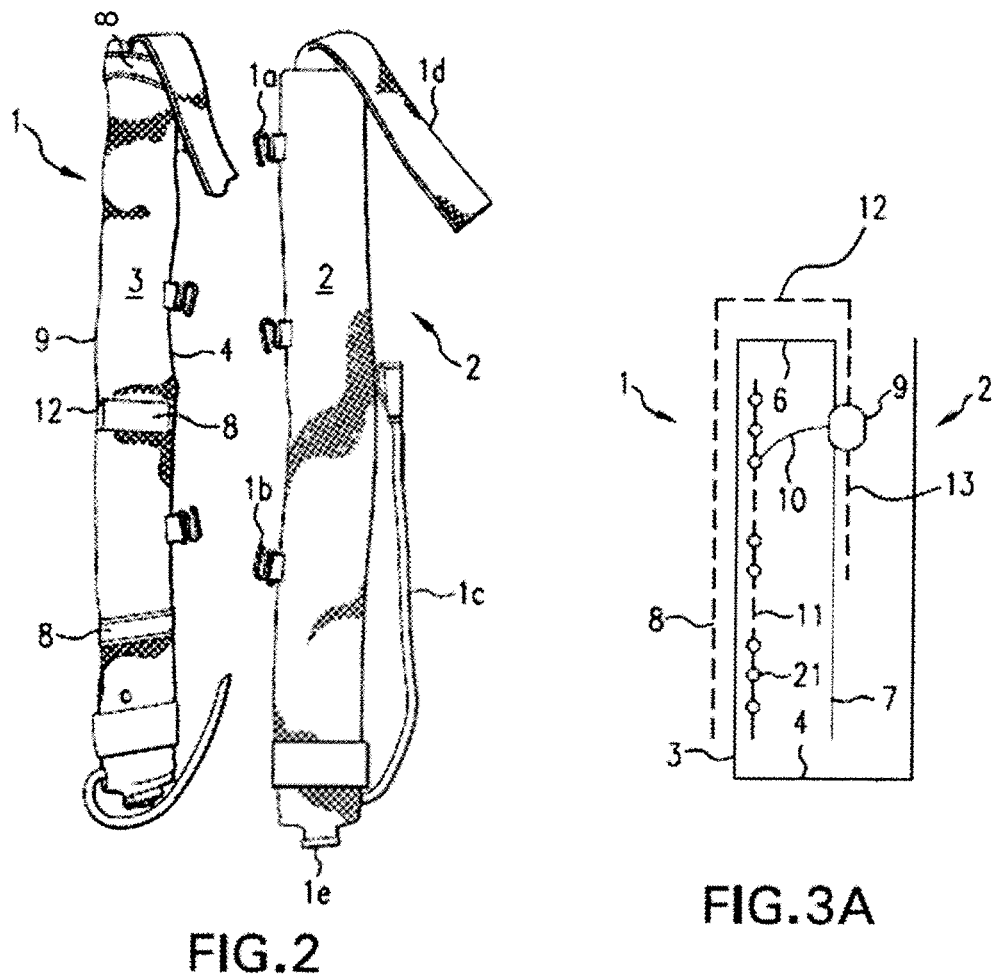
FIG.2
FIG.3A
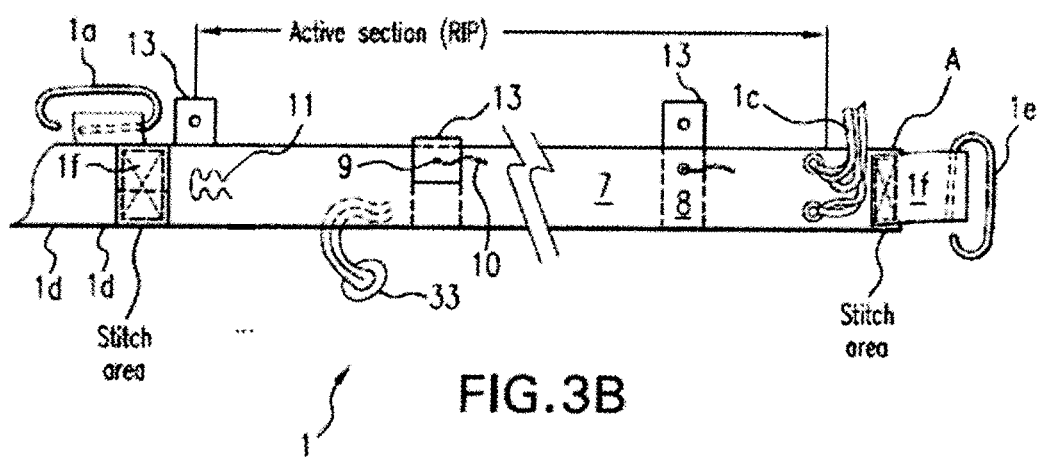
FIG.3B

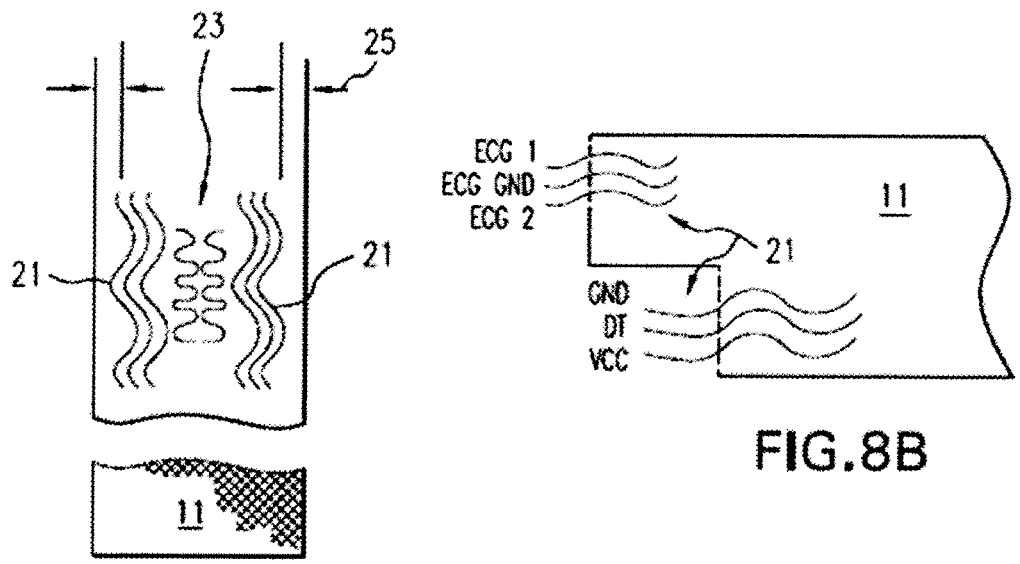
FIG.8A
FIG.8B
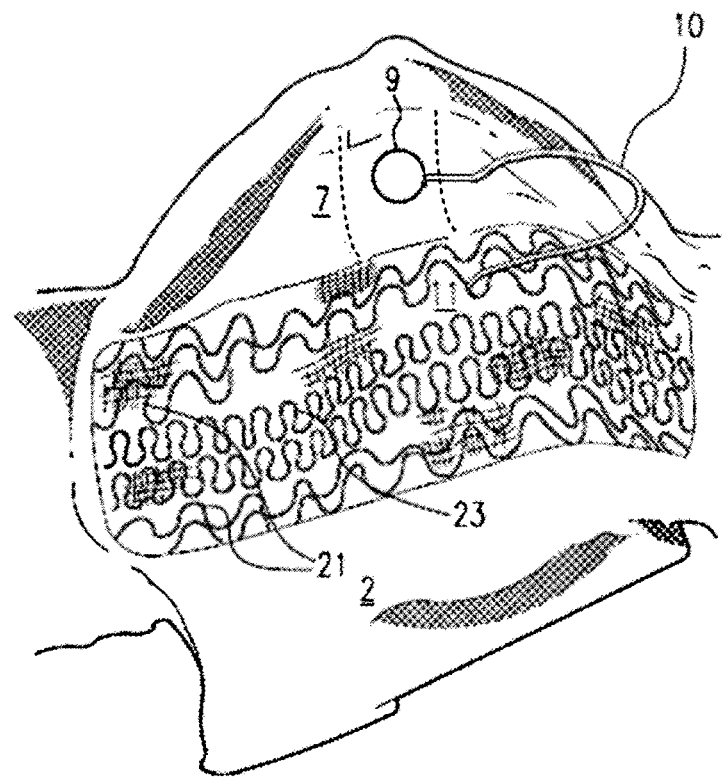
FIG.8C

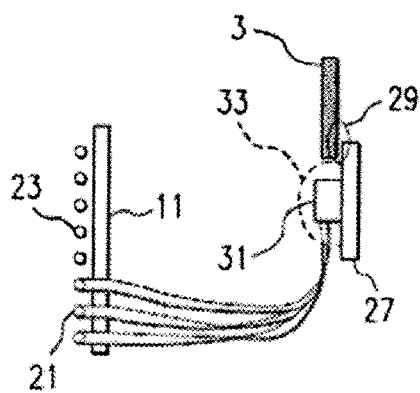 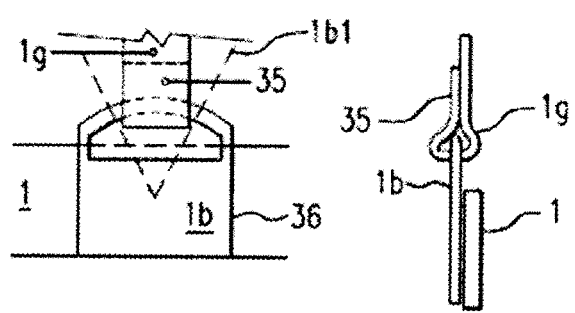
FIG.9  FIG.10A  FIG.10B
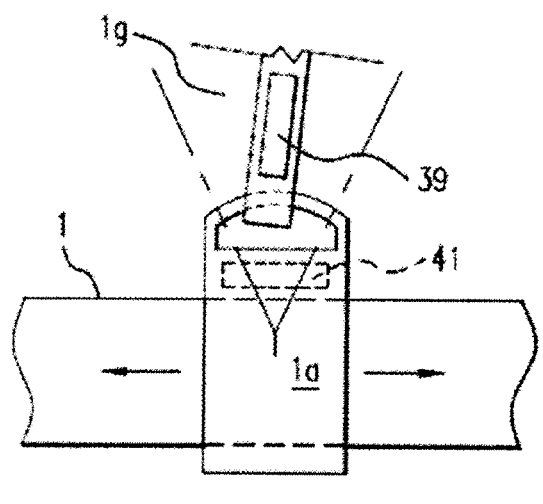 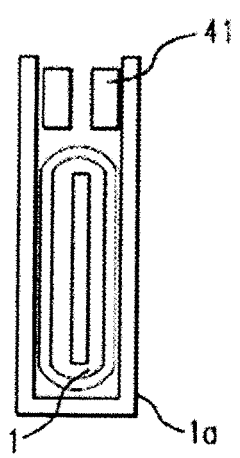
FIG.11A  FIG.11B

BAND-LIKE GARMENT FOR PHYSIOLOGICAL MONITORING

CROSS REFERENCE TO RELATED APPLICATIONS

This application is a continuation of U.S. application Ser. No. 11/586,026, filed Oct. 24, 2006, which is a continuation-in-part of U.S. application Ser. No. 11/233,317, filed Sep. 21, 2005, now U.S. Pat. No. 8,034,001, which claims priority from U.S. Provisional Application Nos. 60/699,698, filed Jul. 15, 2005, and 60/611,900, filed Sep. 21, 2004; and claims priority from U.S. Provisional Application No. 60/730,890 filed Oct. 26, 2005. Each of these patents and applications are incorporated by reference herein in their entireties for all purposes.

FIELD OF THE INVENTION

This application relates to ambulatory physiological monitoring, and particularly to garments for ambulatory physiological monitoring that provide or incorporate a plurality of physiological sensors.

BACKGROUND OF THE INVENTION

Ambulatory physiological monitoring has many applications in sports, medicine, industry and the military. In all these applications, it is advantageous to configure sensors on an comfortable, unobtrusive garment to be worn by a monitored individual.

Among the known technologies for physiological monitoring is inductive plethysmography ("IP"). IP applied to respiratory monitoring, respiratory IP ("RIP"), has been shown to be a reliable and robust monitoring technology. RIP devices and processing methods are described in U.S. patents and US patent applications including: U.S. Pat. No. 6,047,203 issued Apr. 4, 2000; U.S. Pat. No. 6,551,252 issued Apr. 22, 2002; and U.S. patent application Ser. No. 10/822,260 filed Apr. 9, 2004. These patents are included by reference herein in their entireties for all purposes.

Known physiological monitoring garments have been configured in the form of clothing for significant portions of a subject's body, such as shirts, pants, and the like. Known clothing items of such type are not advantageous in certain applications of physiological monitoring, for example, in situations where strenuous activity is possible or when personal garment size fitting is not possible.

SUMMARY OF THE INVENTION

Objects of this invention include providing physiological monitoring garments that are suitable for subjects that can engage in strenuous exertion. The garments of this invention cover only limited sections of a subject's body, and further are easy to use, add little weight, are easy to don and remove.

The garments of this invention are preferably configured as bands or straps that encircle portions of an individuals torso, e.g., a portion of the chest, and carry or incorporate sensors for physiological monitoring tasks such as monitoring respiration, heart rate, and the like. Preferred garments have integrated ECG electrodes and incorporate RIP ("respiratory inductive plethysmographic") sensors. Sensors are optionally arranged into an active section of the garment.

The band-like garments of this invention preferably include one (optionally more than one) straps, e.g., over-the-shoulder straps, that provides increased stability on a wearer.

Associated electronics modules for, e.g., sensor signal processing and telemetry, are preferably mechanically isolated from the band-like garments to further improve garment stability. These modules can be carried on other items of clothing, e.g., a belt.

Band-like or strap-like garments of this invention can readily by configured for a subject and/or accommodate a subject of a range of body sizes, body shapes, and body types. Preferably, a garment has an adjustment portion linked to a single-size active portion. The adjustment portion serves to adapt the single-sized active portion to particular wearers so that is fits snugly about a subject. A garment also preferably includes one or more over-the-shoulder straps; the straps are linked to the band with buckles that permit free angular motion and allow lateral adjustment along the band.

Band-like or strap-like garments of this invention have a simple, easily made, and economical construction. In a preferred embodiment, a band is constructed from a length of fabric material that is folded and arranged so as to serve as a backbone which protects sensors within pockets or folds or carries sensors attached to exterior surfaces RIP is the preferred technology for sensing respiratory function. A garment can directly incorporate RIP sensor conductors into the materials of which it is constructed or can support a material in which these conductors are incorporated. RIP sensors are generally band-like materials extending throughout substantially all the active section of a band and preferably carry RIP sensor conductors and supplementary conductors that can serve as leads for additional sensors. (Other similarly lengthwise extended sensors can also include supplementary conductors to use as leads.) A preferred RIP sensor is described in U.S. patent application Ser. No. 11/233,317, filed Sep. 21, 2005. Alternatively, other length sensitive respiratory sensors can be used along with or in place of RIP sensors.

A band preferably includes sensors for at least one-lead of ECG signals. ECG sensor can be conductive electrodes in direct contact with the subject that have such physical, conductive and moisture handling properties so as to obtain sufficient electrical contact occurs without the use of special conductive gels and the like and to be comfortable and unobtrusive to the subject. Preferred electrodes use conductive cloth-like material optionally mounted on an pillow of elastic foam-like material. Other sensors can include: alternative cardiac sensors: thermistors for measuring skin temperature; microphones in contact with the wearer for responding to sounds generated in the wearer's body; accelerometers for measuring position and activity.

Further aspects and details and alternate combinations of the elements of this invention will be apparent from the following detailed description and are also within the scope of the inventor's invention.

BRIEF DESCRIPTION OF THE DRAWINGS

The present invention may be understood more fully by reference to the following detailed description of the preferred embodiment of the present invention, illustrative examples of specific embodiments of the invention and the appended figures in which:

FIG. 2 illustrates an example of a preferred band-like garment;

FIG. 3A-C illustrate further details of a band-like garment and of a preferred embodiment of an ECG electrode;

FIG. 8A-C illustrate views of an exemplary RIP sensor for use in this invention;

FIG. 9 illustrates a preferred mounting for a skin temperature sensor;

FIG. 10A-B illustrate one preferred buckle arrangement;

FIG. 11A-B illustrate another preferred buckle arrangement;

DETAIL DESCRIPTION OF THE PREFERRED EMBODIMENTS

References to elements in the figures are identified by numerals and by abbreviations, e.g., "ADJ". Numerals and abbreviations are used consistently throughout the figures; only their first use is specifically identified.

Figure 1A:
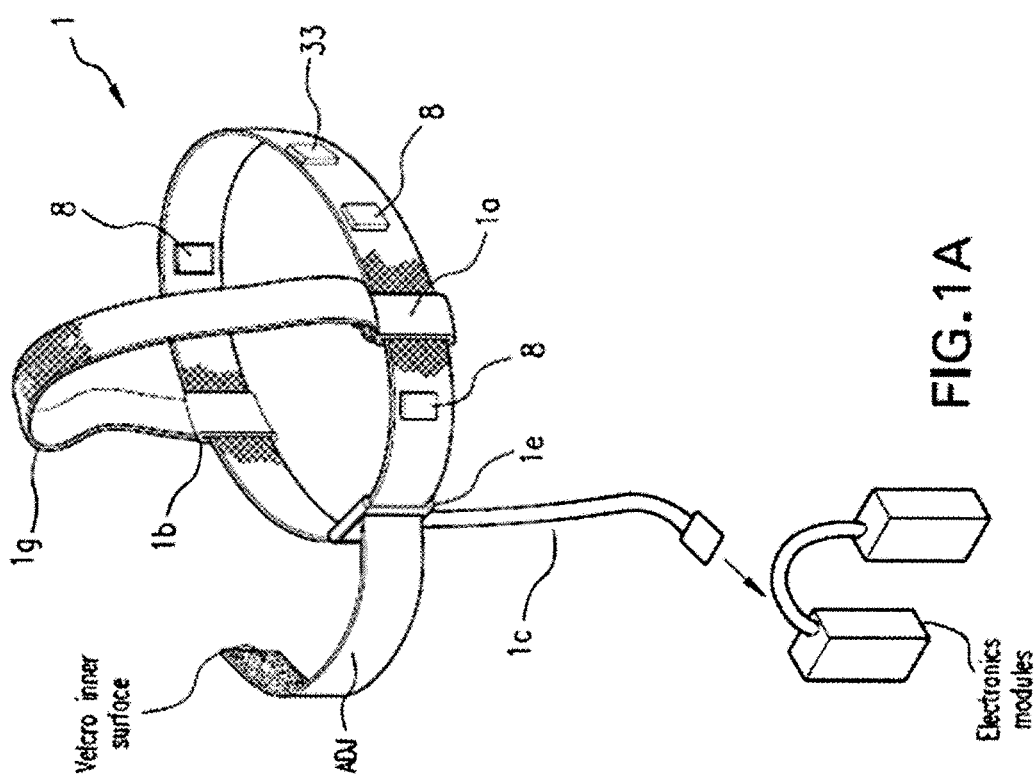
FIG. 1A-B illustrates preferred band-like garments of this invention.

FIG. 1A generally illustrates an angled view of an example of a preferred embodiment of a band-like (or a strap-like) physiological monitoring garment 1 of this invention (also referred to herein as a "HRT" strap). The garment comprises a flexible band of limited width and of sufficient length to encircle the torso of a monitored subject. It includes at least one adjustment section ("ADJ") and one or more active sections ("ACT"). The active sections provide for one or more physiological sensors that can be carried on the band, or can be integral to the band, or can be directly incorporated into the fabrics and other materials of the band. For example, sensors can be carried on a band in pockets, or fastened to a surface (e.g., by sewing, by adhesive, by snaps, by Velcro® strips, and so forth), or otherwise supported by a band. Sensors can be directly incorporated into active portions of a band by weaving, knitting, crocheting, or the like into the fabrics used in these portions, or by being within polymer structures that are integral to the active portions, or by other means.

In the band of FIG. 1A, that active sections, which are largely within the left-half of the band, include two active ECG electrodes 8 and one ECG ground electrode 8 (and/or third party cardiac sensors); one or more skin temperature sensors 33; and respiratory sensors. The ECG electrodes illustrated are mounted on the inner surface (that is the surface facing inward toward the subject) of the band by, e.g., sewing, or adhesive, or the like, so that they are in direct contact with the subject's skin. In preferred embodiments, they include flexible, conductive portions (e.g., a conductive cloth), and can be vertically ("VERT") mounted (e.g., perpendicular to the long axis of the band), or horizontally ("HORIZ") mounted (e.g., parallel to the long axis of the band), or at another orientation. Here, ECG sensing electrodes are vertical while ECG ground ("GND") electrodes are horizontal. In preferred embodiments, the respiratory sensors are directly incorporated into the materials of the band and so are not readily visible in FIG. 1A. Other band embodiments can provide for additional sensors or for different sensors.

Sensor signals are received and processed, e.g., digitized and filtered, by associated electronic circuitry, that, in preferred embodiments, is carried by the monitored subject by being, e.g., carried on the band itself, or carried on another garment worn concurrently with the band, such as in a pouch or pocket of a shirt, or clipped to a belt, or the like. A preferred embodiment of such electronic circuitry is described in U.S. provisional patent application 60/791,005 filed Apr. 10, 2006. Thereby, the present invention can be part of a complete ambulatory physiological monitoring system. FIG. 1A illustrates two such electronics modules which are coupled to the sensors of the associated band by a flexible ribbon cable 1 c with a cloth support and connector (model HR30-10/12), and which are also coupled to each other. Alternatively, sensors and electronic circuitry can be coupled by other varieties of cables, or by a personal wireless link in LAN, or the like. For example, the first module can perform sensor signal processing, and the second module can record or transmit processed data. Alternatively, these and other functions may be housed in a single physical module. Preferred housings and arrangements of associated electronics generally depends on the intended uses of this monitoring garment, e.g., in military applications, in clinical applications, in ambulatory applications, in athletic applications, and the like.

The ADJ section of the band of FIG. 1A, which is largely within the left-half of the band and is illustrated in an open configuration, comprises mating Velcro surfaces that can hold the band at variable lengths so that it can be donned by a subject at a tension sufficient to prevent or limit motion of the band during expected subject activities (in various embodiments, from rest to vigorous activity). One surface threads through buckle 1 e and then folds back. Alternatively, buckles, snaps, ties, and the like, can be used to adjust band length; also, the ADJ sections (or the entire band) can be elastic so that sufficient tension is achieved without the need for adjustment devices. An optional over-the-shoulder strap 1 g extends from an anterior front buckle ("FB") 1 a affixed to the band, over a subject's shoulder, and to a posterior rear buckle ("RB") 1 b affixed to the band, serves to further prevent or limit band motion during expected activities.

Figure 1B:
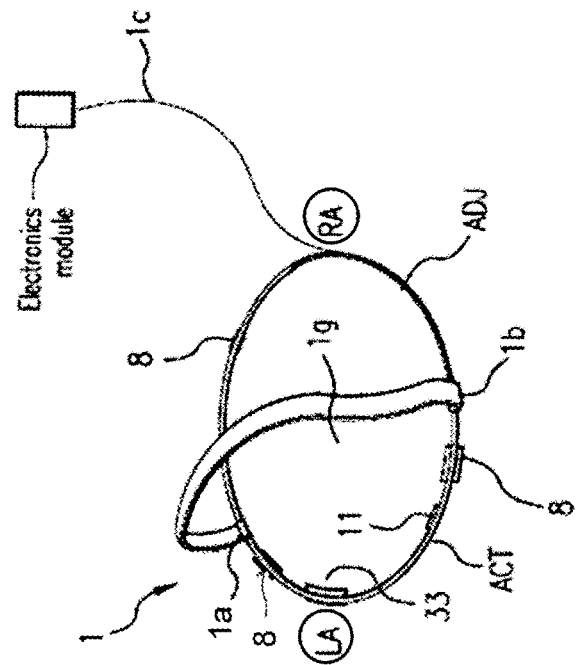

FIG. 1B provides another illustration of the configuration and construction of the exemplary band 1 of FIG. 1A. This figure illustrates how the band-like garment is worn about the chest of a monitored subject, where the resting position of the subject's left arm ("LA") and right arm ("RA") are indicated for reference. The mating Velcro strips of the ADJ section is closed so that the band is held snugly about the chest by the tension adjustment section (ADJ). The band is further stabilized by the over-the-shoulder strap 1 g that extends over the subject's left should from the FB 1 a to the RB 1 b. ECG sensor electrodes 8 are positioned anterior on the band's inner surface to contract the left and right anterior chest, and an ECG ground electrode is positioned posterior also on the bands inner surface. The active section of the band contacts the posterior, the left lateral, and the anterior chest and includes a schematically-illustrated respiratory inductive plethysmographic ("RIP") sensor 11 that is incorporated into the posterior, the left lateral, and the anterior sections of the band. Skin temperature sensor 33 is mounted on the band's left lateral inner surface. Conductors 1 c to an external electronics module connect to the band at one end of the adjustment section (indicated by "A").

FIG. 2 illustrates a outer-surface and an inner-surface of a lengthwise-extended, example of a preferred band 1 of this invention, which affords further appreciation of the configuration and construction of the preferred embodiments of this invention. The inner surface 3 of this embodiment carries three ECG electrodes 8, two of which are ECG sensors, the third being an ECG ground. Also visible are outer surface 2 with FB 1 *a* and RB 1 *b*. This band also incorporates a RIP sensor band (not visible) that is 26 in. long in a relaxed condition. The adjustment section here includes a strip of webbing 1 *d* which can be fixed at various lengths through buckle 1 *e*. Other methods of connection of the webbing and the band, such as plastic snap connectors, are also suitable. Alternatively, the webbing can include an elastic section that is permanently fixed to both ends of the bands' active section. A connection from the band's sensors to external circuitry, such as electronic modules, is provided here by thin, rope-like cable 1 *c* linked to a plug-like connector. Alternatively and as illustrated in FIG. 1A, this connection can be provided by a ribbon-like cable, preferably an flexible cloth-backed ribbon cable. Folds at 4 and 9 are discussed with respect to FIG. 3A.

Figure 3C:
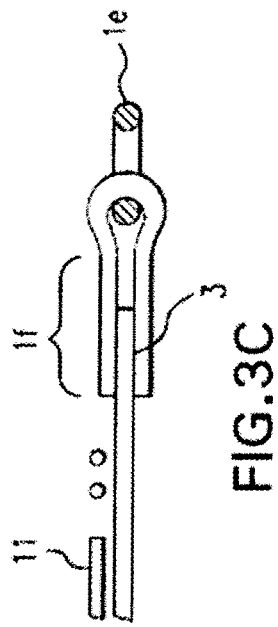

FIGS. 3A-C illustrate further details of one preferred embodiment of the band-like garments of this invention. FIG. 3A illustrates a transverse cross section through an active section of a preferred band, such as the band illustrated in FIGS. 1A-B and 2, at the position of a vertically-mounted flexible ECG electrode, e.g., the electrode adjacent to reference numeral 12. The backbone of a band of this embodiment is an elongated length of flexible, preferably fabric, material that is twice folded back onto itself along the longitudinal axis. Backbone material is represented in FIG. 3A by the thick, solid, black line. Tracing along the backbone folding pattern in detail, the backbone material first forms outer surface 2, then is folded back onto itself along longitudinal axis 4, then forms inner surface 3, then is folded back onto itself again along longitudinal axis 6, and then finally forms inner flap 7 positioned between inner face 3 and outer face 2. ECG electrode 8 is folded along with the supporting material. RIP sensor 11 is further described later. The backbone material preferably has a comfortable feel, is breathable, is washable, is resistant to sweat and skin microorganisms, has properties suitable for continuous use in vigorous activity, including and so forth. The backbone material is optionally elastic. Nylon fabric is a generally suitable backbone material, Polartech, or Underarmour, or similar fabrics, are more preferred.

FIG. 3B illustrates a view of inner flap 7 of an active portion and of an adjacent adjustment portion. Portions of three ECG electrodes 8 are illustrated: "ECG1", "ECG2" and "ECG-GND". FIGS. 3A and 3B together make clear that the flexible ECG electrode materials are affixed to inner surface 3, are folded back at axis 12, and continue and are affixed to inner flap 7. Electrical contact with the ECG electrodes is then made by button-like conductive elements 9 (preferably of a type known as "mini-anorak") which are affixed to electrode tabs 13 and which anchor conductive leads 10. This construction has the advantage that the only exposed portion of the ECG electrode material faces and is in contact with the subject; the remaining portions of the electrode material, the connecting buttons, and the electrical leads are in a recess between inner flap 7 and outer surface 2 and so are protected from external damage.

A portion of flap 7 is cutaway at the left of FIG. 3B so that RIP sensor 11 is apparent between the inner surface fabric 3 and the flap fabric 7 (see also FIG. 3C). A RIP sensor must contract and expand with the subject's respiratory and cardiac movements, and must therefore be able to accommodate relative length changes, preferably, up to approximately 20-40% (or 5-10 in. for a band of 30 in. rest length). Accordingly, the RIP sensor is preferably elastic, for example, incorporating Spandex, Lycra, or other elastic filaments into a fabric backbone, and is mounted on the backbone material so length changes are not restricted. Alternately, the backbone fabric is also elastic and contract and expand along with an incorporated RIP sensor.

The illustrated band also carries skin temperature sensor 33. Sensor 33 along with its connecting leads are illustrated here, for clarity only, as being held away from the band-like garment; normally sensor 33 is carried on the inner surface of the band. Bands can also include additional sensors. For example, third party cardiac sensors (e.g., from Polar, Inc.) provide heart rate information, by producing electromagnetic bursts upon detecting heart beats which can be inductively received by a wire pick-up coil. Illustrated here are connectors for carrying such a third party sensor on the band.

This illustrated band is donned by a subject and fit snugly by pulling a tongue of webbing, 1 *d* in FIGS. 2 and 3B, through (and back through) buckle 1 *e*. Other connectors can be used in place of buckle 1 *e*. An end of an optional over-the-shoulder strap can be fixed at front buckle 1 *a*.

FIG. 3C illustrates a preferred attachment of buckles, loops, and similar fixtures to a band-like garment. A short length of attachment material, such as webbing material, is threaded through the loop, is folded over a portion of a band, and is then both ends of the attachment material are sewn through the band material is region 1 *f*. FIG. 3C illustrates loop 1 *e* attached to both surfaces 2 and 3 of backbone material by webbing sewn through the band in region 1 *f* RIP sensor 11 is adjacent to this attachment.

Figure 4A:
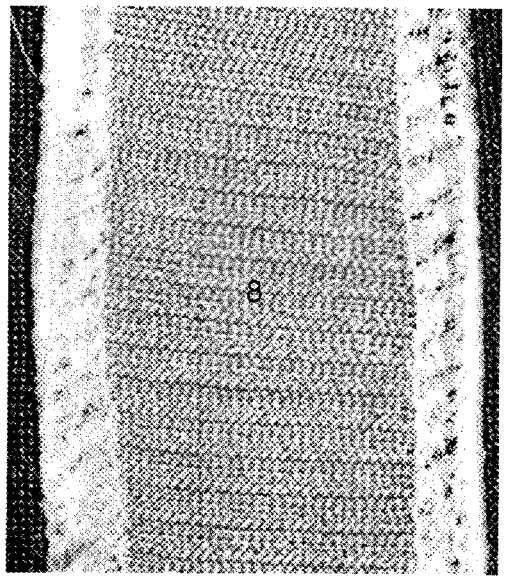
FIG. 4A-B illustrate views of an example of a preferred conductive fabric suitable for ECG electrode.
Figure 4B:
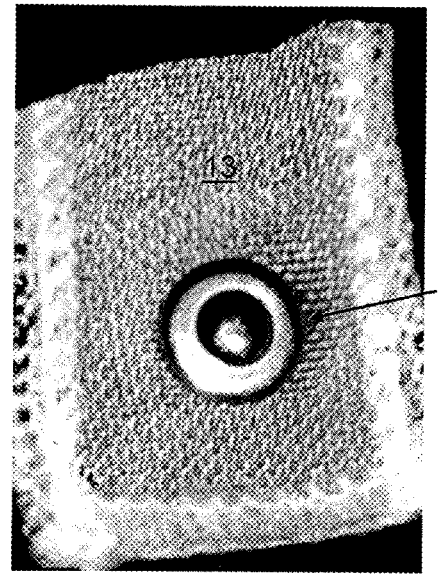
Figure 5A:
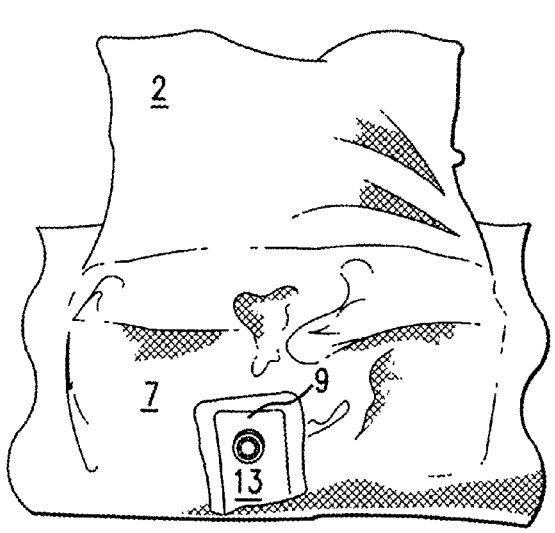
FIG. 5A-B illustrate details of an example of a preferred ECG electrode.
Figure 5B:
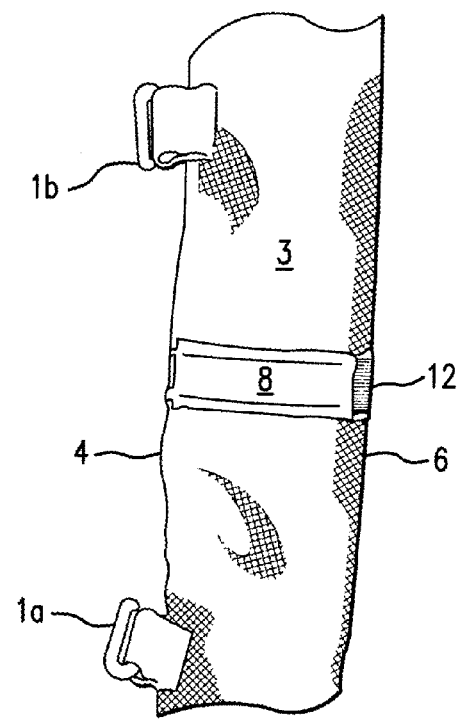
Figure 6A:
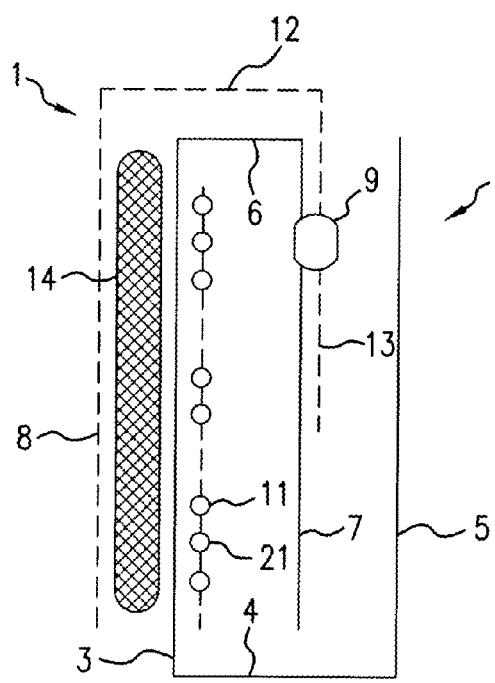
FIG. 6A-B illustrate another preferred embodiment of an ECG electrode.
Figure 6B:
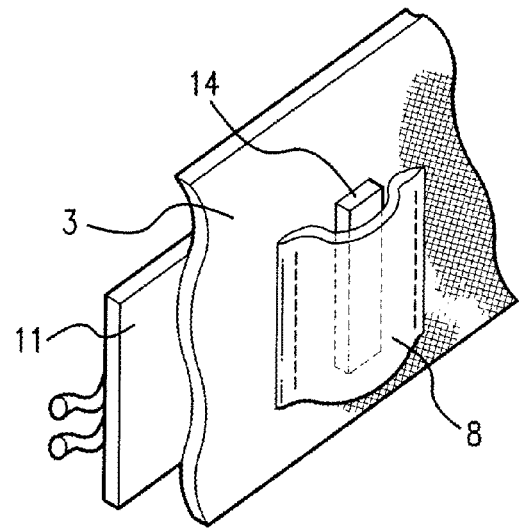

Preferred ECG electrodes are now described in view of FIG. 3A, which illustrates one preferred electrode embodiment; FIGS. 4A-B, which illustrate a preferred, flexible electrode material; FIGS. 5A-B, which illustrate an example of this first embodiment; FIGS. 6A-B, which illustrate a second preferred electrode embodiment; and FIGS. 7A-B, which illustrate a further preferred electrode embodiment.

The preferred ECG electrodes of this invention include flexible highly-conductive material that can establish electrical contact with a subject without the use of conductive fluids, gels, pastes, and the like. The conductive material is usually in the shape of a single, elongated, rectangle or strip that is preferably bounded by a selvage edge. Other shapes, e.g., circle-like, ellipse-like, square-like, and so forth, can be used in different embodiments. Conductive fabrics are suitable electrode materials, and characteristics of preferred conductive fabrics are illustrated in FIGS. 4A-B, which are enlarged views (approximately 4×) of a portion of a conductive strip of an ECG electrode. As illustrated, suitable fabrics are woven (or knitted or the like) from fine conductive fibers such as metal wire or metal-coated fiber, metal-impregnated fiber, and the like. Also, preferred conductive fabrics are unaffected by normal textile processing steps (e.g., weaving, knitting, sewing), have the look and feel of normal textiles when woven or knitted, and are sufficiently durable for at least months of monitoring use. Preferred conductive fabrics are available from Textronics™ Inc., Wilmington, Del.

FIG. 3A illustrates, along with an embodiment of backbone construction, a first preferred electrode construction, where the electrode and conductive fabric strip are represented by the dashed line. This conductive fabric strip is attached (e.g., by sewing) onto a surface of the backbone fabric so that it follows the folding of the backbone. The electrode is exposed 8 on inner surface 3; then is folded 12 back the supporting backbone; then forms a tab-like portion 13 on the surface of flap 7. FIG. 3B also illustrates electrodes 8 hidden on the inner surface 3 and tabs 13 before and after folding back onto flap 7. FIGS. 5A-B also illustrate that electrode 8 is exposed on inner surface 3, and then folded 12 to form a tab-like portion 13 on flap 7.

FIG. 3A also illustrates that signals from a fabric electrode is conveyed externally by conductive snap-type or button-like connector 9 (e.g., a mini-anorak type connector) affixed to the electrode and lead 10 from the button-like connector. As apparent in FIG. 4B (and FIG. 5A), connector 9 directly contacts many conductive fibers in the electrode material; connection to the remaining fibers is mediated by fiber contacts and crossings in the conductive fabric. Lead 10 from the button-like connector 9 is shown in FIG. 8C. Preferably, lead 10 is one of the conductors incorporated in RIP sensor 11, or contacts (e.g., by soldering and the like) one such conductor. RIP sensor 11 is represented in FIGS. 3B and 8A by a dash-dot line, and an exemplary RIP sensor is visible in FIG. 8C. Utilizing RIP sensor conductors for ECG sensor signals (and signals from other sensors) simplifies band construction because then separate leads for sensors need not be installed and because cable 1 *c* then need only connect to conductors of the RIP sensor and not to separate conductors leading to other sensors. Specifically, an ECG electrode signal is carried by a conductor 21 laterally located in the RIP sensor.

FIGS. 6A-B illustrate another preferred embodiment of the ECG electrodes of this invention. This embodiment is substantially similar to the embodiment of FIG. 3A but with the principle exception of the presence of a thin strip of pillow material 14 between the inner surface 3 of a band and an ECG electrode 8 attached to this surface. This underlying pillow material serves to gently urge the electrode into contact with a wearer's skin. The pillow material is preferably, therefore, soft and flexible and, like the backbone cloth, is resistant to sweat and skin microorganisms. To improve electrical contact between then conductive fabric of an electrode and a subject's skin, it is also preferable that the pillow material be moderately water absorptive or retentive. Then, an amount of conductive sweat can be comfortably maintained between the conductive fabric and the subject's skin. Excessive water absorption or retention can lead to certain discomfort due to electrode saturation (especially during vigorous activity), and is thus not preferred.

The choice of backing material generally depends on a balance of fit, structural characteristics, moisture absorption and comfort. Such backing material might be, for example, 6 mm Neoprene polymer, available from Foamorder.com (www.foamorder.com). Others examples include, but are not limited to, Ethylene Propylene Diamine Monomer (EPDM) F-003091, Ethylene Vinyl Acetate (EVA) F-011400, and Neoprene/EPDM/SBR blend F-002032, all available from Armacell (www.armacell.com). While the above examples reference certain commercially available products, it should be kept in mind that other materials may also suffice.

Figure 7A:
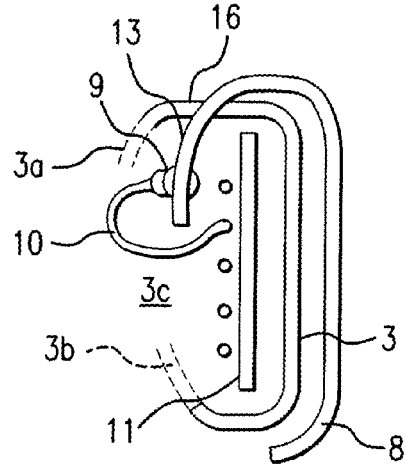
FIG. 7A-B illustrate a further preferred embodiment of an ECG electrode.
Figure 7B:
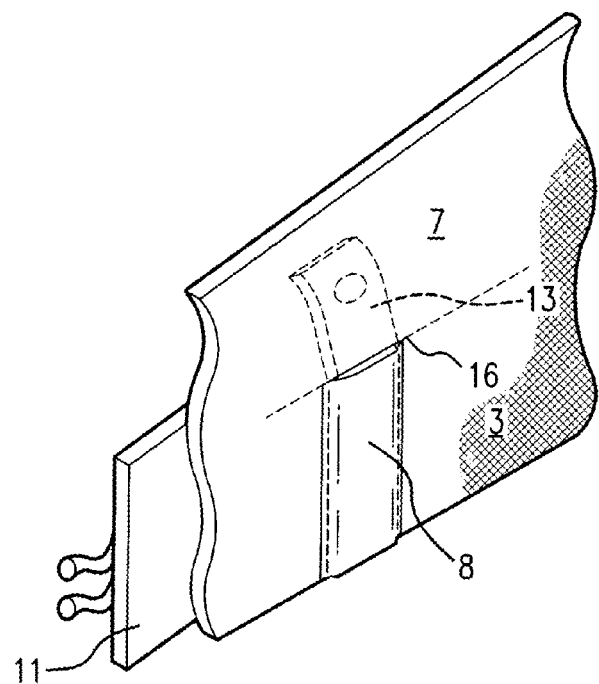

FIGS. 7A-B illustrate another preferred embodiment of the ECG electrodes of this invention which is suitable for another preferred folding pattern of the backbone material. In this embodiment, the backbone fabric is folded to that a single pouch or single recess or single pocket contains both the RIP sensor 11 and the ECG electrodes extensions 13 to which connection is made. FIG. 7A illustrates an exemplary such folding where the fabric inner surface 3 is formed between two longitudinal folds, and where the first flap 3 *a* and second flap 3 *b* of backbone material beyond these longitudinal folds meet each other so that tube-like interior pouch 3 *c* is formed. The ECG electrode is again a single elongated strip of conductive fabric affixed (e.g., by sewing) onto the backbone fabric so that electrode 8 it is exposed on inner surface 3 of the band. The electrode tab for external connection extends into internal pouch 3 *c* through a short slit 16 (the width of the electrode) in the backbone material along one longitudinal fold. Connection to the electrode can be as in the previous embodiment, namely through a button-like connector to a lead derived from one of the RIP sensor conductors.

A further variant is to include, as in FIGS. 6A-B, a strip of pillow-like material between the inner surface of the band and the ECG electrode.

FIGS. 8A-B illustrate an exemplary respiratory inductive plethysmographic (RIP) sensor 11, and FIG. 8C illustrate a portion of an actual example of the RIP sensor similar to the RIP sensor of FIGS. 8A-B. Band-like garments of this invention provide respiratory sensors, preferably RIP sensors. A RIP sensor is held in a protected portion of a band, such as within folds of backbone material as in FIGS. 3A and 6A. The sensor is held so that it is tensioned by adjusting the band about a subject, and so that is moves along with respiratory and/or cardiac motions of the subject's chest. A band may have one or more RIP sensors. If only one RIP sensor is provided, it is preferably substantially the same length as the active section of the band. A band may alternatively include other plethysmographic type sensors based on changes in capacitance, resistance, mutual inductance, or other electrical property (or other property) that occur with changes in length or tension.

FIG. 8A illustrates schematically an exemplary preferred RIP sensor 11 in the form of an elastic band incorporating several conductors. The central portion of the band incorporates unshielded conductors 23 in a repetitive pattern at 5-6 spatial cycles per inch chosen for RIP performance. Laterally from the central RIP conductors are groups of conductors 21 in a repetitive pattern at 2-3 spatial cycles per inch chosen to limit conductor length and weight. These lateral conductors advantageously provide power and data leads to other sensors. FIG. 8B illustrates an exemplary use of lateral conductors 21: a first ECG sensor (ECG 1), a second ECG sensor (ECG 2), an ECG ground sensor (ECG GND), a lead for data from another sensor (DT), and power and ground (VCC, GND). Finally, the band is edged with a selvage edge 25. FIG. 8C illustrates a band constructed to be substantially similar to the band of FIG. 8A. Preferred RIP sensors are further described in U.S. patent application Ser. No. 11/233,317, filed Sep. 21, 2005, which is incorporated by reference herein in its entirety.

Bands of this invention can provide for additional physiology or physiology-related sensors, one example being an accelerometer and another being a skin temperature sensor. FIG. 9 illustrates an embodiment of a skin temperature sensor 33. Sensor 33 includes thermistor or more fully integrated temperature sensor 31 (e.g., proportional-to-absolute-temperature (PTAT) type circuitry) in an eline-type package which is bonded to metallic disk using thermally-conductive epoxy 27. The disk is sewn, glued, or otherwise bonded at 29 on the subject-facing surface of inner side material of a band. Lead wires to the thermistor skin temperature sensor are derived for a lateral group of conductors 21 of a RIP sensor 11, and are attached to the sensor by, e.g., soldering. The thermally conductive disk with supported thermistor and lead wires are coated for protection.

A band/strap garment of this invention and (optional) over-the-shoulder strap can be comfortably worn by subject's with a range of check sizes. First, as described, a band/strap garment is provided with an adjustment section for adjusting the band's length about a subject's chest. Second, as now described, the over-the-shoulder strap and its mountings flexibly accommodate to a range of chest sizes. Preferably, the over-the-shoulder strap itself is made of flexible materials and has an adjustable length so subject awareness of the strap is limited or minimal. For example, length adjustment means can be at the front or back buckle attachments. Also the front and back buckles that attach the over-the-shoulder strap permit attachment of a over-the-shoulder strap at adjustable positions on a band, and also permit free angular movement of an over-the-shoulder strap that is fixed to the buckles.

FIGS. 10A-B illustrates a plain view and a cross section of a preferred structure for rear buckle 1 *b* (see also FIGS. 1A-B). The rear buckle is stitched to band 1 and provides an attachment site for over-the-shoulder strap 1*g*. The preferred attachment site permits the terminal portion of the over-the-shoulder strap to move freely through angle indicated at 1 *b* 1. In the illustrated embodiment, such angled movement is possible because opening of the rear buckle, through which the terminal portion of the over-the-shoulder strap passes, is larger than the terminal portion and has a curved shape which is convex towards band 1. The terminal portion of the over-the-shoulder strap passes through the buckle of the rear buckle, and then folds and is held to the over-the-shoulder strap by Velcro, snaps, or other attachments suitable for fabric materials.

FIGS. 11A-B illustrates a preferred structure for front buckle 1 *a* (see also FIGS. 1A-B). The front buckle has an opening structured similarly to the opening of rear buckle 1 *b* so that the over-the-shoulder strap can move freely in the front buckle through indicated angle. The terminal portion of the over-the-shoulder strap is affixed to the front buckle by being folded back after passing through the buckle's opening being held by Velcro, snaps, or other attachments suitable for fabric materials.

However, front buckle 1 *a* is not permanently fixed to band-like garment 1, but can instead be adjusted back-and-forth along the band. Such adjustment is indicated in FIG. 11A. FIG. 11B illustrates that the front buckle has a U-shape that surrounds band 1 (illustrated as backbone fabric material enclosing a sensor, such as a RIP sensor). The legs of the U-shaped front buckle extend above the band and can be affixed to each other above the band by Velcro 41, snaps, or other attachments suitable for the buckle material. When the tops of the legs are not attached to each other, the buckle can freely move back-and-forth along band 1, but when the legs are attached, the buckle pinches the band is held in position. Alternatively, the tops of the legs are permanently attached (e.g., by adhesive) so that the buckle can be slid into a position from which it cannot readily move. A U-shaped portion of a front buckle can be plastic, fabric, and so forth. The width of the FB (indicated as "FBW") sufficient to limit adverse effects that the buckle may have on sensors incorporated into or carried by a band.

Figure 12:
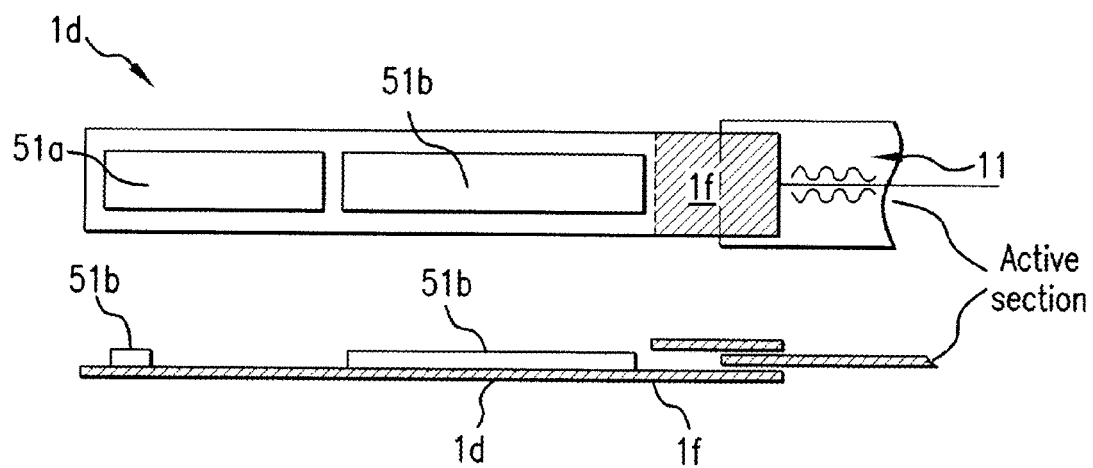
FIG. 12 illustrates a preferred adjustment section.

FIG. 12 illustrates plain and side views of details of a preferred adjustment portion. At the right of the band-like garment is the active section with RIP sensor 11. The left includes the adjustment portion 1 *d* (including, e.g., a webbing-type fabric material) which is passed through loop 1 *e* (FIGS. 2, 3B) and then folded back and attached to itself so that the band-like garment is held at a selected length. The adjustment-section webbing is fixed to the active section by preferably sewing 1 *f*. In the illustrated embodiment, the adjustment-section webbing is attached to itself by mating Velcro strip 51 *a*, after it has passed through buckle 1 *e*, with Velcro strip 51 *b*, that has not passed through buckle 1 *e*.

Figures 13A, 13B:
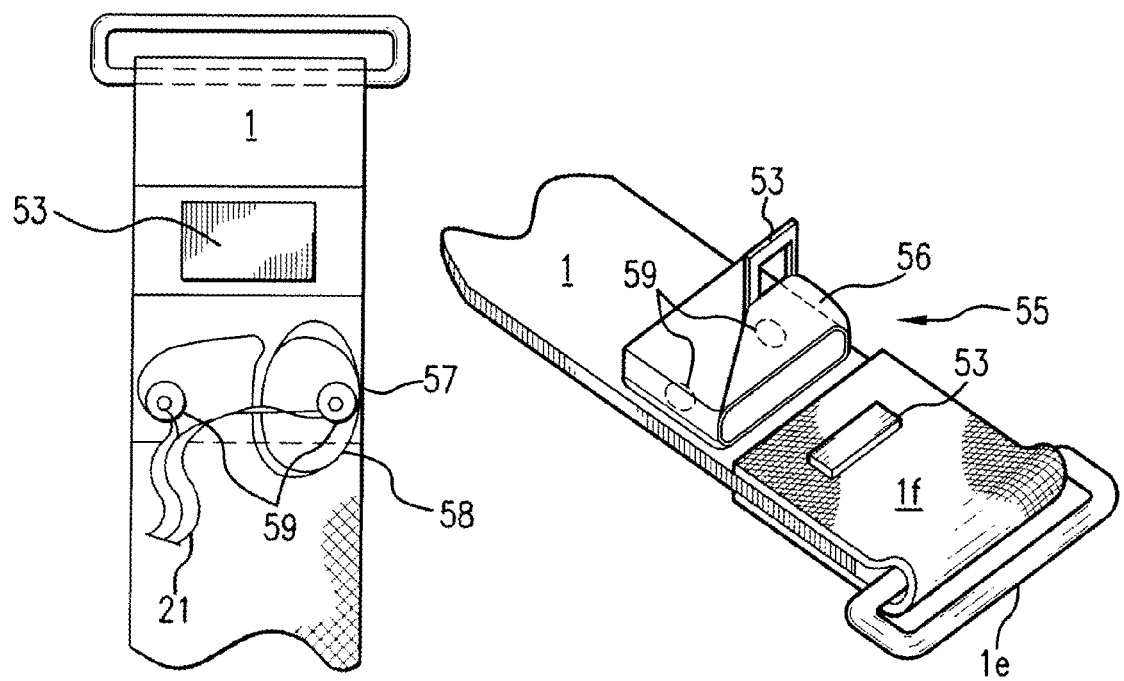
FIG. 13A-B illustrates alternative sensor attachments.

FIGS. 3A, 6A and 8C illustrate preferred attachments for ECG electrodes of this invention to leads derived from RIP sensor bands. FIGS. 13A-B illustrate attachment of alternative cardiac sensors. Alternative sensors may be attached and carried by a band/strap garment of this invention by various means including adhesive; sewing, Velcro, snaps, and the like. FIG. 13B illustrates a pouch 44 for holding and carrying one or more sensors. The pouch is in turn attached to and carried by band 1. It can be sized to accommodate one or more alternative cardiac sensors (or types of physiological sensors). It can optionally include a flap-like top 56 for holding and protecting sensors carried in the pouch. In this embodiment, top 56 is held against band 1 by mating Velcro strips 3. Also illustrated is buckle 1 *e* for an adjustment section and attached by webbing to band 1 by sewing 1 *f*.

FIG. 13A illustrates various alternative approaches to linking alternative cardiac (and other) sensors to leads derived from a RIP sensor band. In one approach, one, two, or more button-like conductive elements 59 (preferably of a type known as "mini-anorak") are linked to lateral conductors 21 incorporated into a RIP sensor band, e.g., in a manner similar to that illustrated in FIG. 8C and are attached to similar button-like conductive elements 59 interior to pouch 55. Sensors in the pouch can contact elements 59 and thereby to lateral conductors 21. Another approach is suitable for sensors that signal detected events by emitting a burst of electromagnetic fields which can be inductively received. Loop 58 is such an inductive receiver including loops of wire the ends of which are linked to button-like conductive elements 59 and then to leads 21 derived from a RIP sensor band. For sensors known in the art as "Polartech", a suitable receiver includes 10 to 14 loops of AWG 26 wire. In this approach, button-like conductive elements within carrying pouch (59 in FIG. 13B) are not directly connected to a sensor. Alternatively, both approaches can be combined when sensors include at least one sensor of each type.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference for all purposes. Further, none of these references, regardless of how characterized above, is admitted as prior to the invention of the subject matter claimed herein.

What is claimed is:

1. A physiological monitoring garment comprising:
   an active portion comprising a respiratory inductive plethysmographic band, the respiratory inductive plethysmographic band comprising a first conductor; and
   an electrocardiogram electrode electrically coupled to the first conductor, the electrocardiogram electrode comprising:
      a first portion mounted on the garment such that the electrocardiogram electrode contacts a wearer wearing the garment.

2. The garment of claim 1, further comprising an electrical contact coupling the first conductor with an area of a second portion of the electrocardiogram electrode.

3. The garment of claim 2, wherein the electrical contact comprises a first fastener portion connected to the first conductor, and a second cooperating fastener portion connected to the second portion of the electrocardiogram electrode.

4. The garment of claim 2, the garment having a first configuration wherein the electrical contact is exposed, and having a second configuration wherein the electrical contact is not exposed.

5. The garment of claim 1, wherein a surface area of the first portion of the electrocardiogram electrode is larger than a surface area of the second portion of the electrocardiogram electrode.

6. The garment of claim 1, wherein the first conductor is coupled to an additional physiological sensor.

7. The garment of claim 1, the respiratory inductive plethysmographic band further comprising a second conductor coupled to an additional physiological sensor, wherein the first conductor comprises a respiratory inductive plethysmographic conductor.

8. The garment of claim 7, wherein the first conductor is arranged in a wave pattern with a spatial frequency of between 5 and 6 cycles per inch, and wherein the second conductor is arranged in a wave pattern with a spatial frequency of between 2 and 3 cycles per inch.

9. The garment of claim 1, wherein the electrocardiogram electrode further comprises an electrically conductive cloth configured to contact a skin of the wearer.

10. The garment of claim 1, the electrocardiogram electrode further comprising a pillow portion disposed between the garment and the second portion of the electrocardiogram electrode, such that the first portion of the electrocardiogram electrode is pressed against a skin of the wearer.

11. The garment of claim 1, further comprising an adjustment section attached to an end of the active portion and configured such that the garment may be fit snugly on the wearer.

12. A physiological monitoring garment comprising:
an active portion comprising a fabric material;
a respiratory inductive plethysmographic band disposed on the fabric material and comprising a first conductor and a second conductor,
wherein the first conductor is arranged in a wave pattern with a spatial frequency of between 5 and 6 cycles per inch, and
wherein the second conductor is arranged in a wave pattern with a spatial frequency of between 2 and 3 cycles per inch; and
an electrocardiogram electrode electrically coupled to one of the first and second conductors, the electrocardiogram electrode comprising:
a first portion mounted on the garment such that the electrocardiogram electrode contacts a wearer wearing the garment.

13. The garment of claim 12, further comprising an electrical contact coupling the first conductor with an area of a second portion of the electrocardiogram electrode.

14. The garment of claim 13, wherein the electrical contact comprises a first fastener portion connected to the first conductor, and a second fastener portion connected to an area of the second portion of the electrocardiogram electrode.

15. The garment of claim 12, wherein a surface area of the first portion of the electrocardiogram electrode is larger than a surface area of the second portion of the electrocardiogram electrode.

16. The garment of claim 12, wherein the first conductor is a respiratory inductive plethysmographic conductor.

17. The garment of claim 12, wherein the first conductor is a respiratory inductive plethysmographic conductor and the second conductor is coupled to an additional physiological sensor.

18. The garment of claim 12, wherein the electrocardiogram electrode further includes an electrically conductive cloth configured to contact a skin of the wearer.

19. The garment of claim 12, the electrocardiogram electrode further comprising a pillow portion disposed between the garment and the second portion of the electrocardiogram electrode, such that the first portion of the electrocardiogram electrode is pressed against a wearer's skin.

20. The garment of claim 12, further comprising an adjustment section attached to an end of the active portion such that the garment may be fit snugly on the wearer.

21. The garment of claim 12, wherein the adjustment section includes a tensioning belt to encircle a torso of the wearer.

* * * * *